(12) United States Patent
Fontayne et al.

(10) Patent No.: US 6,551,275 B2
(45) Date of Patent: Apr. 22, 2003

(54) GRID SHEATH FOR MEDICAL INSTRUMENT

(75) Inventors: Diego Y. Fontayne, Montebello, NY (US); Steven Bellofatto, Closter, NJ (US); Edward J. Kaplan, Boca Raton, FL (US)

(73) Assignee: Integrated Implant Systems, LLC, Arlington, VA (US)

( * ) Notice: Subject to any disclaimer, the term of this patent is extended or adjusted under 35 U.S.C. 154(b) by 0 days.

(21) Appl. No.: 09/858,669

(22) Filed: May 17, 2001

(65) Prior Publication Data

US 2002/0103457 A1 Aug. 1, 2002

Related U.S. Application Data

(60) Provisional application No. 60/265,075, filed on Jan. 31, 2001.

(51) Int. Cl.$^7$ ................................................ A61M 5/00
(52) U.S. Cl. .............................. 604/116; 600/8; 606/1
(58) Field of Search .............................. 600/1–8, 436, 600/455–464; 128/920, 922; 604/57, 59, 54, 64, 62, 117, 116, 135; 606/1, 130

(56) References Cited

U.S. PATENT DOCUMENTS

| | | | |
|---|---|---|---|
| 3,704,707 A | 12/1972 | Halloran | |
| 4,267,149 A | 5/1981 | Bruckner et al. | |
| 4,400,170 A | 8/1983 | McNaughton et al. | |
| 4,451,254 A | * 5/1984 | Dinius et al. | 206/535 |
| 4,700,692 A | * 10/1987 | Baumgartner | 600/7 |
| 4,838,265 A | 6/1989 | Cosman et al. | |
| 5,242,373 A | 9/1993 | Scott et al. | 600/7 |
| 5,305,203 A | 4/1994 | Raab | |
| 5,366,896 A | 11/1994 | Margrey et al. | |
| 5,514,101 A | 5/1996 | Schulz et al. | |
| 5,609,152 A | 3/1997 | Pellegrino | |
| 5,860,909 A | 1/1999 | Mick et al. | 600/7 |
| 5,871,448 A | 2/1999 | Ellard | 600/459 |
| 6,002,859 A | 12/1999 | DiGioia, III et al. | |
| 6,007,474 A | * 12/1999 | Rydell | 600/7 |
| 6,102,844 A | 8/2000 | Ravins et al. | |
| 6,129,670 A | 10/2000 | Burdette et al. | |
| 6,132,358 A | 10/2000 | Glenn et al. | |
| 6,206,832 B1 | 3/2001 | Downey et al. | |
| 6,214,013 B1 | 4/2001 | Lambrecht et al. | |
| 6,267,718 B1 | 7/2001 | Vitali et al. | |
| 6,270,472 B1 | * 8/2001 | Antaki et al. | 600/7 |
| 6,387,034 B1 | 5/2002 | Lee | |
| 6,432,035 B1 | 8/2002 | Ravins et al. | |

FOREIGN PATENT DOCUMENTS

WO          9722379          6/1997

* cited by examiner

*Primary Examiner*—Teresa Walberg
*Assistant Examiner*—Thor Campbell
(74) *Attorney, Agent, or Firm*—Heller Ehrman White & McAuliffe LLP

(57) ABSTRACT

A grid sheath that holds a medical instrument in place in order to insert treatment seeds into a patient. The grid sheath includes a sheath unit in which the medical instrument is fitted therein, whereby the medical instrument is capable of sliding movement within the sheath unit. The grid sheath also includes at least one plate support rod, which is preferably adjustable and that is integral with a distal end of the sheath unit. The grid sheath further includes a push plate, that is integral with a distal end of the plate support rod. When the medical instrument is placed in position with respect to a grid template, the medical instrument is engaged with a needle in a hole of the grid template, and the push plate rests against a distal surface of the grid template. As the medical instrument is actuated to deposit seeds and thereby to move away from the grid template to deposit more seeds in another position within the patient, the push plate provides for registration of the medical instrument with respect to the grid template while this is occurring.

12 Claims, 10 Drawing Sheets

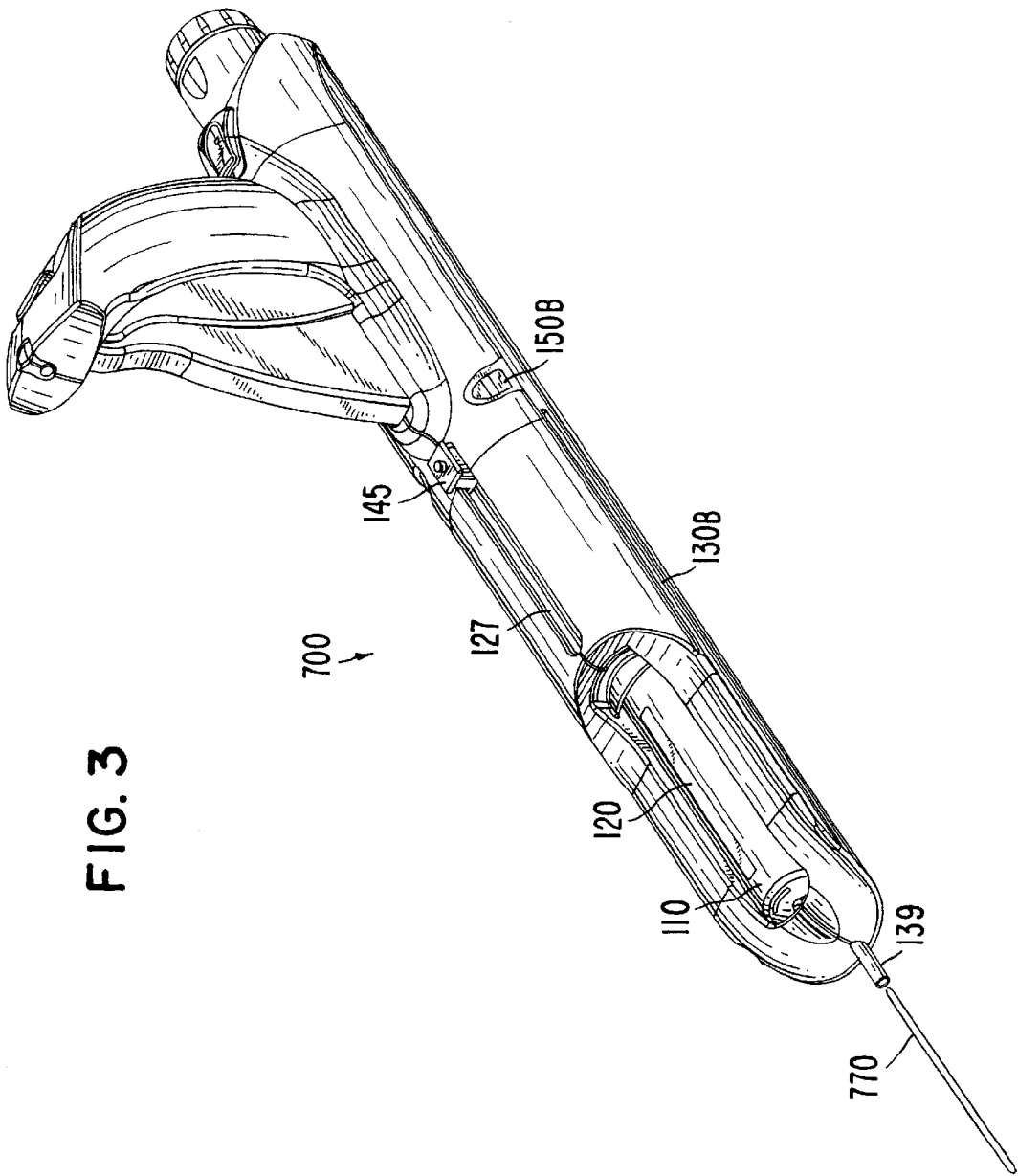

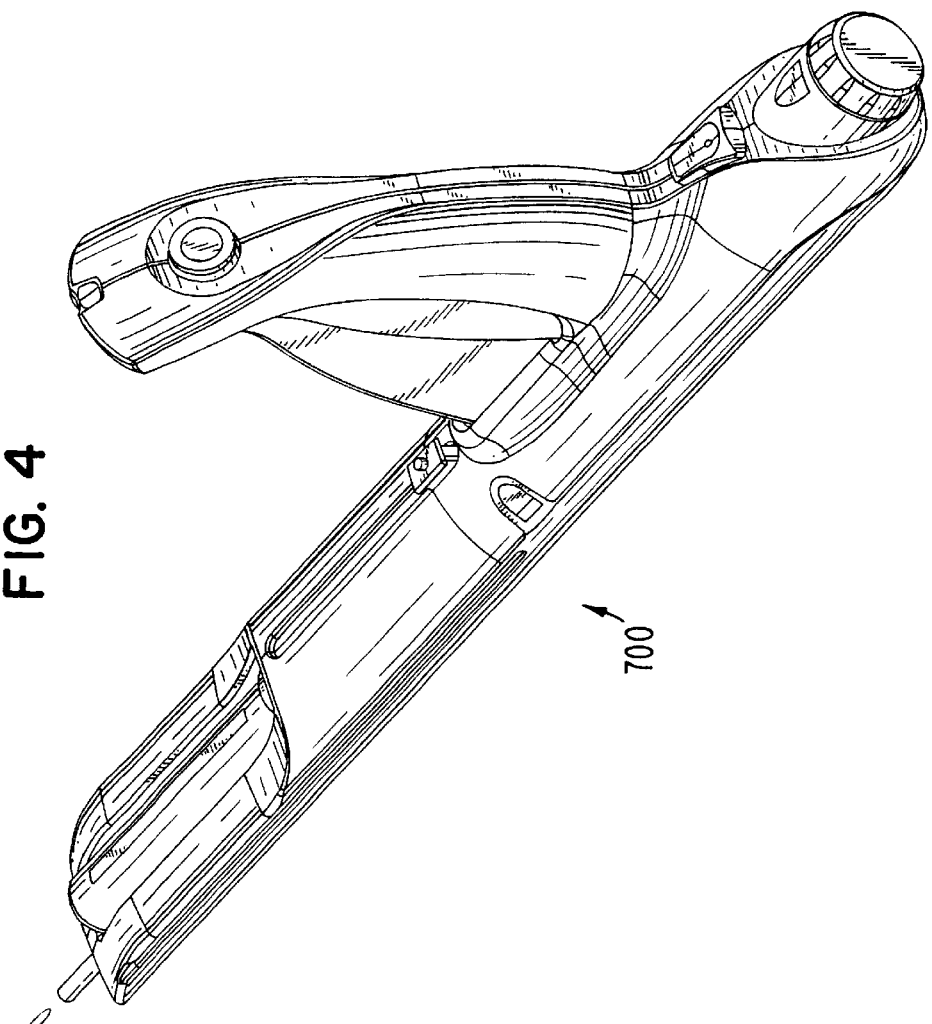

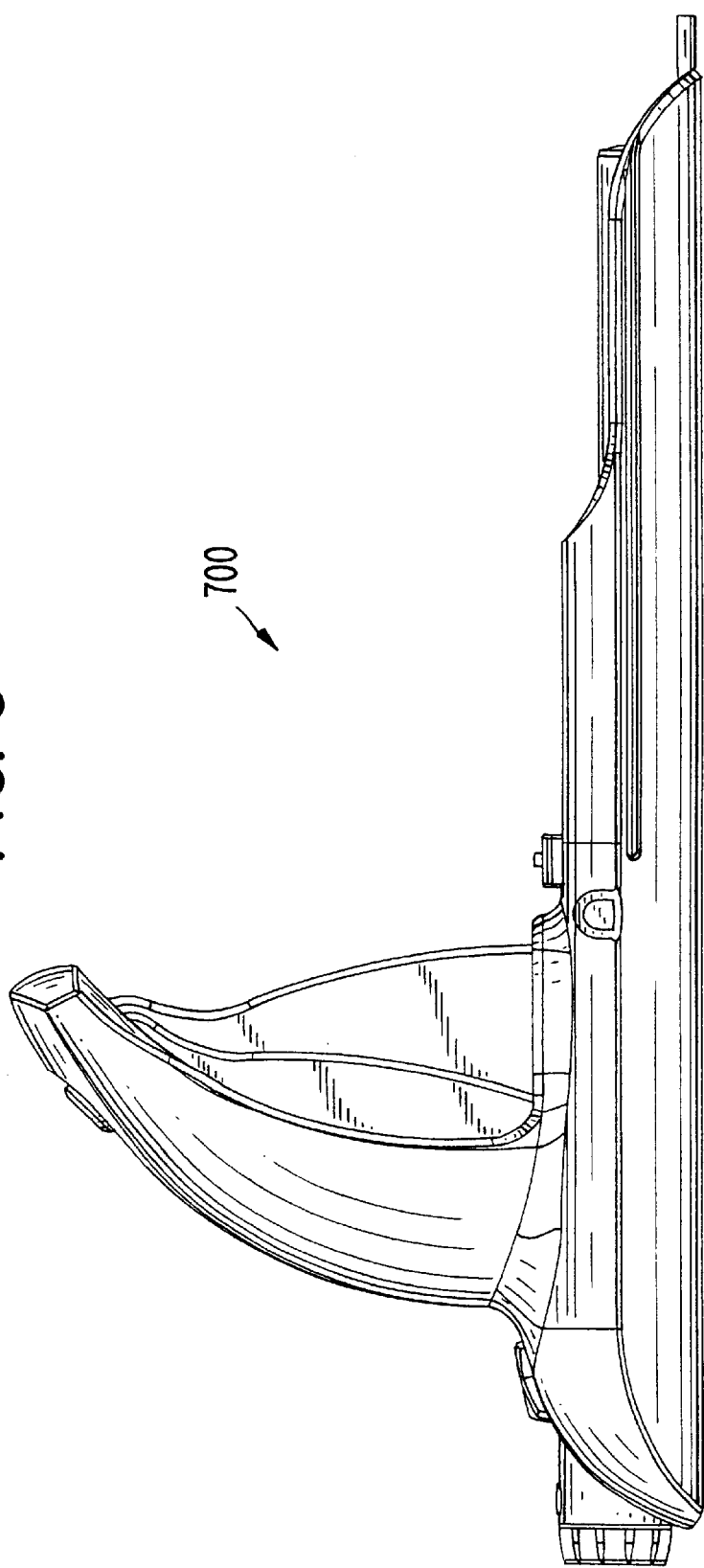

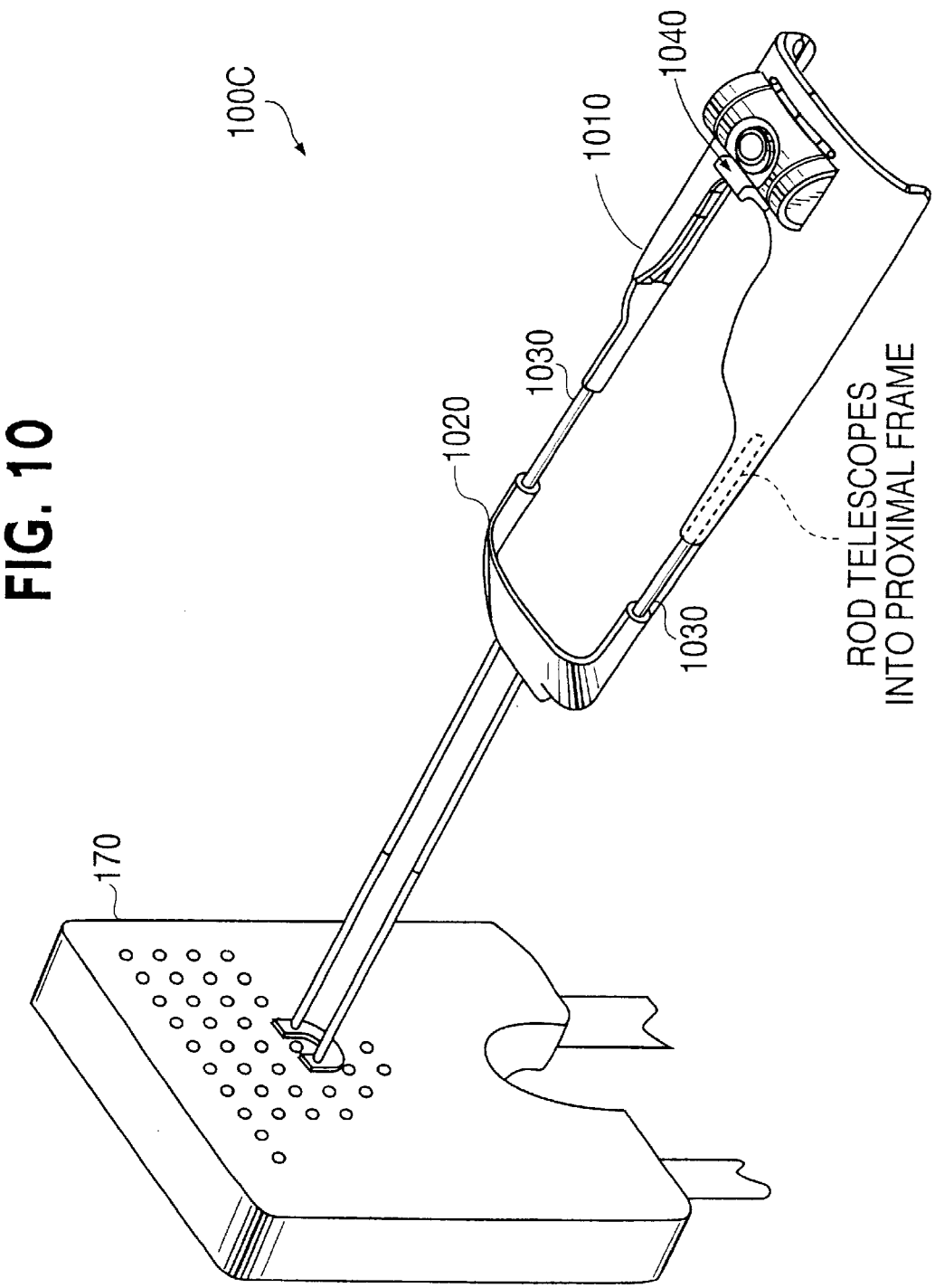

GRID SHEATH FOR MEDICAL INSTRUMENT

This Application claims priority to U.S. Provisional Application 60/265,075, filed Jan. 31, 2001, which is incorporated in its entirety herein by reference.

BACKGROUND OF THE INVENTION

1. Field of the Invention

The present invention relates to a grid sheath for a medical instrument that is used to assist in implanting seeds, such as radioactive seeds, into a patient's body. In particular, the present invention relates to a grid sheath used to couple to a medical instrument that implants radioactive seeds into a patient's prostate gland, for example, in order to treat prostate cancer.

2. Description of the Related Art

For treating prostate cancer, radioactive seeds are provided to various locations within a patient's prostate gland, by way of a medical instrument, also called a seed implantation device. Typically, a base unit which includes an ultrasound unit is used to determine the exact location of the patient's prostate gland with respect to the base unit. FIG. 9 shows a base unit 912 with a grid template 170 mounted to it. The ultrasound unit of the base unlit 912 includes a probe 915, which is inserted into the patient's rectum while the patient is lying on his back. The grid template 170 is mounted onto the base unit via extendible rods 914, whereby the grid template includes a plurality of rows and columns of holes in which a needle can be inserted. Typically, the grid template includes 13 by 13 matrix of needle holes, where adjacent holes on a row or column are 5 mm apart. Every other row is labeled with a number, and every other column is labeled with an alphabetic character. There is a direct relation between the center line axis of the ultrasound probe and the position of the holes of the grid template. The base unit 912 is capable of moving either inwards or outwards with respect to the patient.

A needle is provided through a hole on the grid template, and then inserted into a region within the patient's body in which the prostate gland is located. By using the ultrasound unit, a precise position of the proximal and distal positions of the prostate gland can be determined and recorded. The distal position of the prostate gland is also called the "zero retraction plane". Once that information is recorded, a pre-plan can be determined by a doctor, where the pre-plan corresponds to a plan for injecting seeds into particular locations within the patient's prostate gland. Such treatment is generally started by placing the needle at the zero retraction point, and then applying seeds with respect to that reference point.

For a conventional seed implantation device, a needle is first placed into a particular hole of the grid template, and then the seed implantation device is held in place by a doctor and attached to the needle. The seed implantation device is then used to inject one or more seeds into the patient's body through the needle. When finished with that hole, the seed implantation device is deattached from the needle, and placed aside. Then, the needle is removed from the grid template, and a new needle is positioned at another hole of the grid template, according to the specific pre-plan for treating the patient's prostate gland. Alternatively, all the needles can be placed in holes of the grid template in advance. One such conventional seed implantation device is called a MICK applicator, and requires the operator to physically reposition the MICK applicator proximally in order to place subsequent seeds.

With these conventional devices, there is no way to automatically move the instrument back while it is attached to a needle on the grid template.

SUMMARY OF THE INVENTION

The present invention provides a grid sheath for a seed implantation device that is used to provide seeds to the patient via a needle coupled to a front portion of the seed implantation device, so as allow a doctor to easily hold a medical instrument in its proper place while performing the seed implantation. The grid sheath adapts to the seed implantation device to allow automatic advancement of the needle relative to the grid template.

According to one aspect of the invention, there is provided a grid sheath for a medical instrument. The grid sheath includes a sheath unit configured to couple to the medical instrument, and to allow the medical instrument to move relative to the sheath unit. The grid sheath also includes at least one plate support rod that is coupled to a distal end of the sheath unit. The grid sheath further includes a push plate that is coupled to a distal end of the at least one plate support rod. The push plate is configured to abut against a girid template to allow an operator to manually operate the medical instrument while maintaining the medical instrument in a particular x, y location with respect to the grid template.

According to another aspect of the invention, there is provided a grid sheath for a medical instrument. The grid sheath includes a sheath unit configured to couple to the medical instrument, and to allow the medical instrument to move relative to the sheath unit. The grid sheath also includes at least one plate support rod that is coupled to a distal end of the sheath unit. The grid sheath further includes a push plate that is coupled to a distal end of the at least one plate support rod. The medical instrument has a needle nozzle that allows for a needle to be engaged with the medical instrument. The at least one plate support rod is of a size such that the push plate is not in contact with the grid template when the needle is engaged with the medical instrument. Either the plate support rod is capable of being lengthened to make the push plate be in contact with a surface of the grid template, or the medical instrument is capable of moving an amount relative to the sheath unit so that the push plate is put in contact with the surface of the grid template.

BRIEF DESCRIPTION OF THE DRAWINGS

The invention will become more fully apparent from the following detailed description when read in conjunction with the accompanying drawings with like reference numerals indicating corresponding parts throughout, and wherein:

FIGS. 2 through 5 show different views of a medical instrument that fits within the sheath unit of the grid sheath, according to the invention;

FIG. 10 shows a top perspective of a grid sheath according to a fifth embodiment of the invention.

DETAILED DESCRIPTION OF THE PREFERRED EMBODIMENTS

Preferred embodiments of the present invention will be described in detail hereinbelow, with reference to the drawings.

The present invention is directed to a grid sheath for coupling to a medical instrument, in particular, a seed implantation device. Details of the medical instrument is the subject of a first related application entitled "MEDICAL INSTRUMENT", U.S. Ser. No. 09/858,658 filed May 17, 2001, which is incorporated in its entirety herein by reference. The medical instrument is configured to receive a seed cartridge, and to remove a seed from the seed cartridge in order to provide the seed to a needle that can be attached to a needle nozzle on a front location of the medical instrument.

A second related application describes details of a targeting fixture on which the medical instrument can couple to, more particularly, to a cradle unit or a sheath unit of the targeting fixture, so as to allow for fully automatic implanting of seeds into a patient, to thereby lessen any errors associated with manually inserting such seeds by the use of a MICK applicator or the like. The second related application is entitled "TARGETING FIXTURE", U.S. Ser. No. 09/858,657filed May 17, 2001. There is also a third related application entitled "TARGETING FIXTURE TO A GRID TEMPLATE", U.S. Ser. No. 09/858,656 filed May 17, 2001, each of which is incorporated in its entirety herein by reference. Details of the seed cartridge is a subject of a fourth related application entitled "CARTRIDGE-MOVEABLE SHIELD", U.S. Ser. No. 09/858,653 filed May 17, 2001, which is incorporated in its entirety herein by reference.

The present invention relates to the use of a hand-held device to position the medical instrument in place with respect to a grid template. This is opposed to the fully automatic positioning of the medical instrument that is performed using, the targeting fixtures of the related applications. Thus, the present invention provides for seed implantation using, some automatic features and some manual (e.g., hand-held) features.

The sheath unit of the grid sheath according to the present invention is similar to the sheath unit of the targeting fixture applications. Like the sheath units of the targeting fixture applications, the sheath unit of the present invention allows the medical instrument to be fitted into place at a proper x,y,z location with respect to a orid template, and also allows for the medical instrument to be attached to a needle placed into a particular hole of the grid template.

The sheath unit preferably includes slots (not shown, but see the description in the second and third related applications). A key way (not shown, but see the related applications) is respectively provided in each of the slots. Each key way is preferably a lubricated plastic part, and juts out of its respective slot in order to engage with a sheath interface slot provided on opposite sides of the medical instrument.

Figure 1:
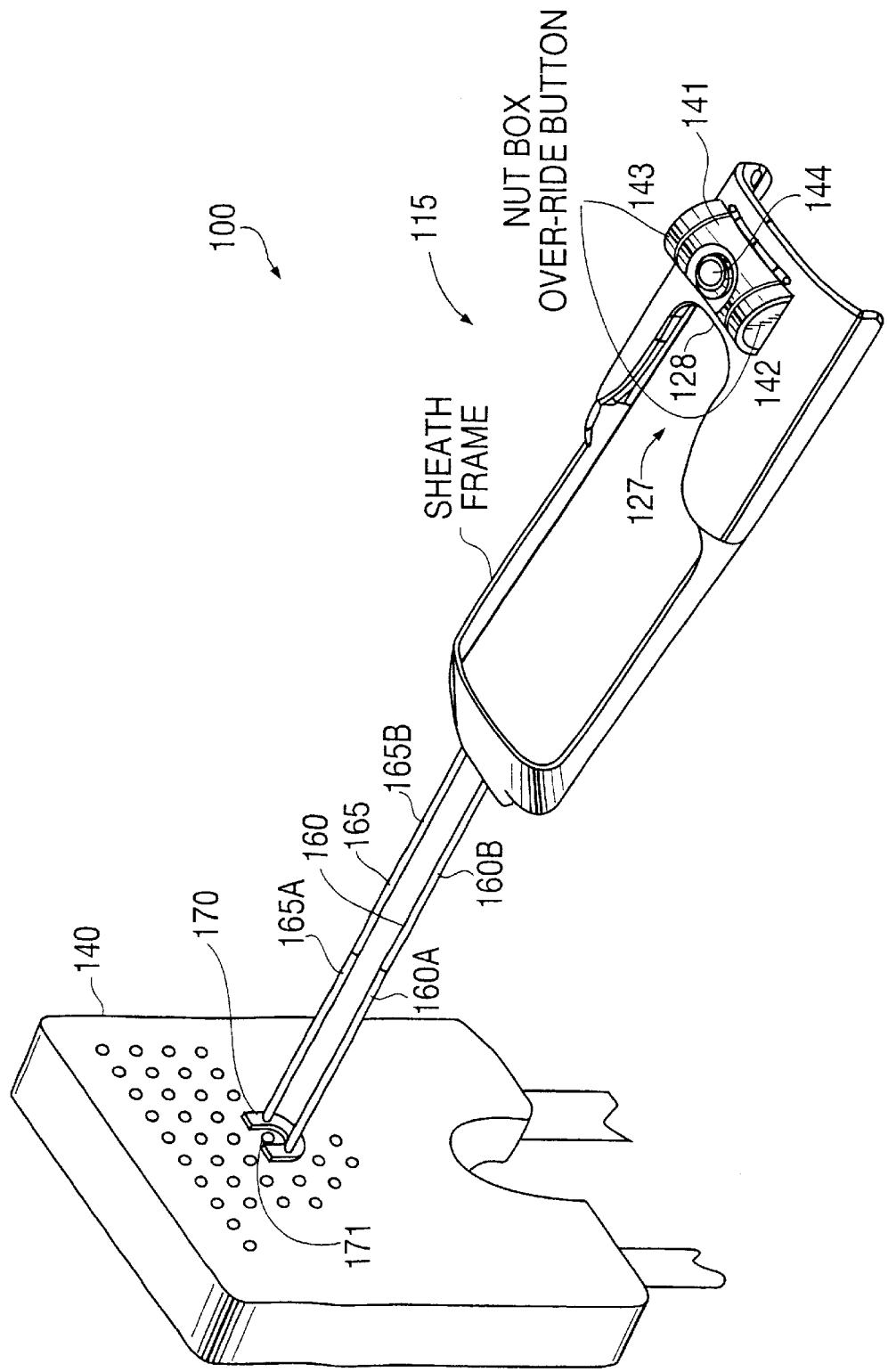
FIG. 1 shows a top perspective view of a grid sheath according to a first embodiment of the invention.

As seen in FIG. 1, the sheath unit 115 of the grid sheath 100 of a first embodiment of the invention has a U-shaped opening 127 at its top portion. This opening 127 allows visual access to the cartridge, to allow the user to read the seed capacity count (see the related Cartridge-Moveable Shield patent application, which describes the seed count feature on the cartridge). The sheath unit 115 has a cylindrical element 141 that is fitted onto its top portion. The cylindrical element 141 is fitted with first and second side buttons 142, 143 and a top button 144. The functions of these buttons will be explained later. In short, the first and second side buttons 142, 143 are simultaneously engaged by pushing both of them inwards, and this action allows a nut box interface disposed on the top of the medical instrument to move. In an alternative configuration, engagement of just one of the buttons 142, 143 allows movement of the medical instrument relative to the sheath unit 115. The nut box interface is described in detail in the related medical instrument and targeting fixture applications (see also FIGS. 2–5 of this application). The nut box interface of the medical instrument couples to an element (not shown) on the bottom of the upper surface of the sheath unit 115, below the buttons 142, 143, 144.

In the present invention, during the pre-plan, a doctor determines the locations of needles to place into a grid template 140. Typically, a plurality of needles will be placed into different holes of the grid template 140 at different depths, where those depths correspond to the deepest position within the prostate that a seed or seeds is to be implanted at a particular x,y location. The doctor typically works his or her way from the top of the grid template 140 to the bottom of the grid template 140, during the seed implantation process.

The medical instrument is held by the doctor and placed within the sheath unit 115. As explained in the related "medical instrument" application, side slots of the medical instrument are fitted onto the key ways of the sheath unit 115, and the medical instrument is slid within the sheath unit 115 in a direction towards the grid template 140. The medical instrument is locked in place when the nut box interface of the medical instrument couples to the element on the underside of the sheath unit 115. In a preferred implementation of the first embodiment, a clicking sound is heard at that time, informing the user that the medical instrument is correctly positioned within the sheath unit 115. This is performed once in a procedure and locked automatically. When the medical instrument is clicked into place, it also engages with the needle disposed within a hole of the grid template 140, by way of the needle nozzle at the front-most portion of the medical instrument, as explained in the related medical instrument application.

When the top button 144 disposed on the cylindrical element 141 of the sheath unit 115 of FIG. 1 is pushed downwards from its normal, upwards position, the nut box interface of the medical instrument disengages from the sheath unit 115, thereby allowing the medical instrument to be removed by sliding it back out of the sheath unit 110. This is done once in a procedure.

Referring now to FIGS. 2 through 5, the medical instrument 700 includes a handle 705 which has an actuator/trigger 180 by which a user can push inwards to eject a seed out of the medical instrument 700 and into a needle 770, and thereby into a patient. The medical instrument 700 is shown as having a cartridge accepting region for accepting a seed cartridge 10 that contains seeds. The cartridge accepting region is located at a portion of the medical instrument 700 adjacent to the needle nozzle 139. The cartridge 110, which includes a seed capacity indicator 120, is the subject of the first related application.

As a seed is fired from the medical instrument 700 and into a patient by way of the needle 770, the medical instrument 700 backs out from the sheath unit 115 in a direction away from the grid template 140. In more detail, as the trigger/actuator 180 on the handle 705 of the medical instrument 700 is engaged by a predetermined amount from its home position, a seed is removed from the seed cartridge 10 by the medical instrument 700, and the seed is pushed into the needle 770. As the user continues to engage the trigger mechanism 180 past the predetermined amount, the medical instrument 700 moves back away from the grid template 140, but remains seated within the sheath unit 115.

As the medical instrument 700 moves backwards in a direction away from the grid template 140, while still seated in the sheath unit 115, the nut box interface 145 moves from its initial location at its most proximal position, to a position that approaches the distal end of the medical instrument 700. In other words, as the trigger/actuator 180 was pressed to move the medical instrument 700 back away from the grid template 140, the nut box interface 145, which is grabbed by an element on the underside of the sheath unit 115, is held in position while the rest of the medical, instrument 700 moves backwards with respect to it. The nut box interface 145 is shown at its most proximal position in FIGS. 4 and 5.

When the user starts to index the medical instrument, the nut box will start moving forward, and it will push against the sheath unit 115 (at or about location 128 in FIG. 1). Since the grid sheath 100 is fixed in space relative to the grid template 100 (due to the push plate 170 being in intimate contact with the grid template 140), the medical instrument will move backwards (away from the grid template 140). The medical instrument will then push against the sheath unit 115, which will in turn push against plate support rods 160, 165, which will in turn push against the pusher plate 170, which will in turn push against the grid template 140. Since the grid template 140 is fixed in space relative to the patient (it is typically disposed on a heavy stand), this will allow the medical instrument to be moved carefully out relative to the grid template 140 in the z-direction, while at the same time the medical instrument is being held and manipulated by the user.

The nut box interface 145 is capable of movement longitudinally within the slot 127 in which it is disposed on the top side of the medical instrument 700, as seen in FIGS. 4 and 5. The slot distance is approximately the depth of a largest prostate gland. The maximum allowable stroke of the medical instrument 700 is determined by this slot distance. Once the medical instrument 700 has moved the entire distance of the slot 127, the nut box interface 145 cannot move any further (since it abuts against the distal end of the slot 127), and the medical instrument 700 has to be reset back into its "zero" position within the sheath unit 115. The resetting is by way of a user pushing against the first and second side buttons 142, 143 in FIG. 1, which releases the nut box interface 145 from a drive screw within the medical instrument (the drive screw is not shown, but see the related medical instrument application) to which it is normally attached, thereby allowing a user to push the medical instrument 700 within the sheath unit 115 back to its most-proximal position with respect to the grid template 140. When the first and second side buttons 142, 143 are released, the nut box interface 145 re-engages with the drive screw. Reset movement of the nut box interface 145 should preferably be performed only after disconnecting the medical instrument 700 from the needle.

Figure 2:
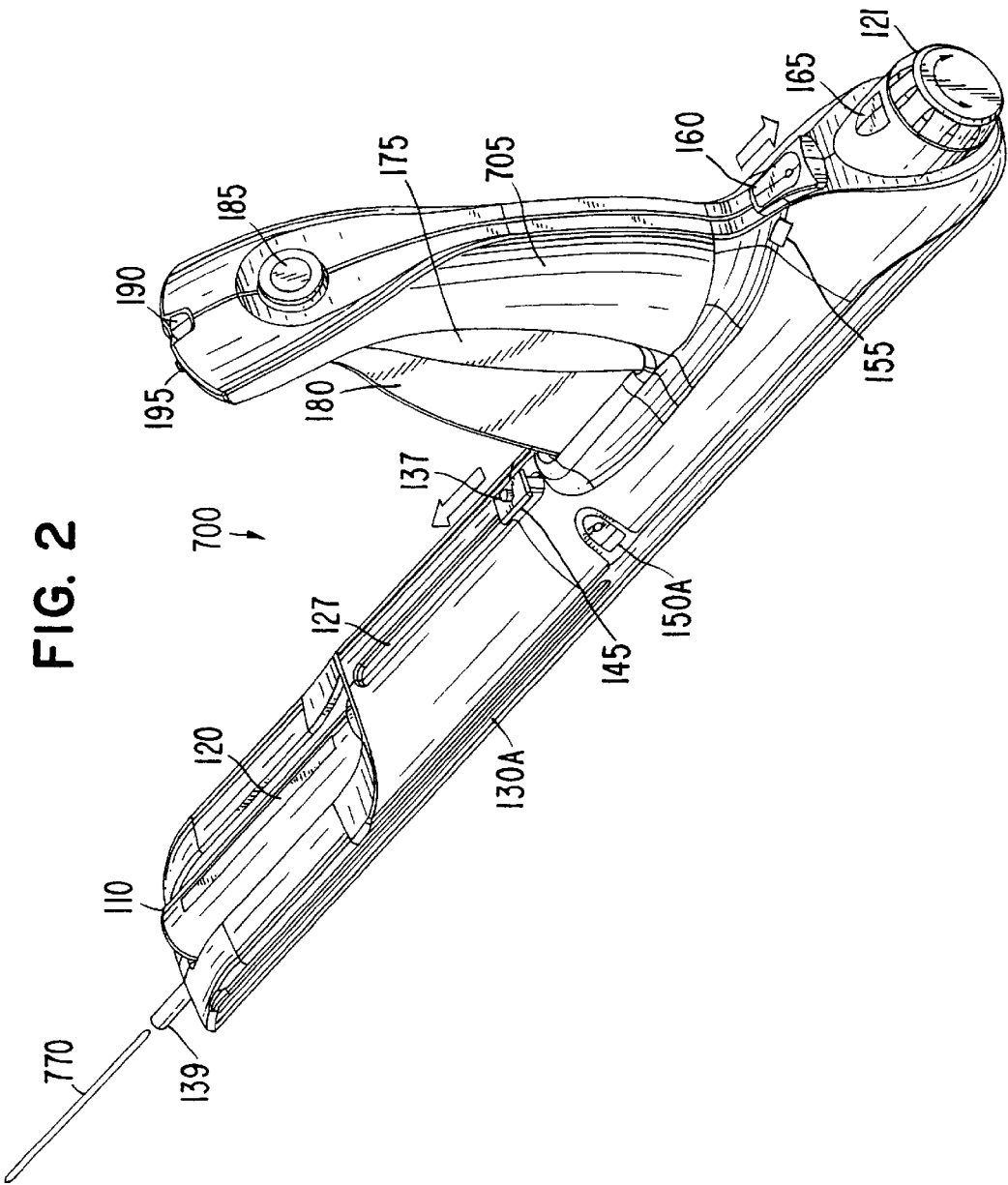

At the proximal end of the medical instrument 700 of FIG. 2 is a pitch adjustment knob 171, which can be set to a position to move the medical instrument 700 backwards by a desired amount to control individual seed implants. The pitch adjustment knob 170 may be moved from position to position between seed firings, based on a particular pre-plan being accomplished during a treatment of a patient. A pitch indication window 165 is provided near the pitch adjustment knob 171, to provide a visual indication to the user of the pitch amount.

Also shown in FIGS. 2 and 3 is a vernier feature 150A, 150B provided on each side of the medical instrument 700. The vernier feature 150A, 150B informs a user as to the exact z-position during a seed-implanting process. In more detail, the vernier feature 150A, 150B corresponds to a 0 to 3" (or metric equivalent) scale provided on both sides of the medical instrument 700, whereby a window slides over a particular numeric indicator on that scale to inform the user as to the depth of the needle with respect to the proximal and distal ends of the prostate gland. In other words, the vernier feature is 150A, 150B informs the user as to how far in the z-direction the medical instrument 700 has moved from the needle initial placement position. FIG. 2 shows the vernier feature 150A in the home, or "0", position.

FIG. 2 also shows a seed counter indicator 190 provided at a top portion of the handle 705, and which counts the number of seeds that have been fired. A counter reset button 195 is provided near the seed counter indicator 190, and when pushed resets the count to "0".

Also shown in FIG. 2 is a cosmetic flapper 175, which defines a start position coincident with the onset of device index movement by which the trigger/actuator 180 moves toward. The nut box interface 145 is shown as having a nut box release trigger 137, which releases the nut box interface 145 from the drive screw when engaged.

At the back portion of the medical instrument 700 there is disposed a needle release 160, which releases a needle coupled to the needle nozzle 139. FIG. 2 also shows a seed transfer command button 185, which causes a seed to be transferred from the seed cartridge 110 to the medical instrument 700.

The coupling of the nut box interface with the drive screw is described in detail in the related application entitled "MEDICAL INSTRUMENT", and will not be discussed herein for sake of brevity.

Referring now to FIG. 1, two parallel-positioned plate support rods 160, 165 are integrally coupled to a distal end of the sheath unit 115. The plate support rods 160, 165 are preferably adjustable in length, such as by having concentrically positioned portions 160A, 160B, 165A, 165B that allow the plate support rods 160, 165 to be telescoped to a particular length (e.g., similar to that used for golf ball retrievers), and whereby a turning movement locks them in place at a particular length. One of ordinary skill in the art will recognize that other types of adjusting mechanisms for the plate support rods may be utilized, while remaining within the scope of the invention as described herein.

A push plate 170 is integrally, coupled to the distal ends of the plate support rods 160, 165. The push plate 170 and the plate support rods 160, 165 are preferably metal components that can be autoclaved so as to be sterilized for reuse. All elements of the sheath unit 115 are preferably autoclavable as well. Alternatively, other embodiments may include a design consistent with a disposable sheath unit. In these alternative embodiments, for example, the frame of the grid sheath may be plastic, while the plate support rods are metal.

The push plate 170 is shown as having a U-shape, whereby the U-shape allows the push plate 170 to be positioned around a particular hole of the grid template 140, such as hole 171. Though not shown in FIG. 1, a needle would be positioned at a particular depth within the hole 171. With the needle in place on the grid template 140, the grid sheath 100 according to the invention would then be placed so as to couple the medical instrument with the needle. The plate support rods 160, 165 are initially in their fully-retracted position. The grid sheath 100 is moved into place to be engaged with a needle on the grid template 140. Due to the plate support rods 160, 165 being fully retracted, the push plate is not in contact with the grid template. Typically, the needle will be -manually held in place while it is engaged with the medical instrument, so that it will be at the correct distance so as to start inserting seeds into the patient. Once the medical instrument is mated with the needle, the plate support rods 160, 165 are lengthened from their fully retracted position, so that the push plate 170 is placed in intimate contact with the surface of the grid template 140 that faces the medical instrument.

With the medical instrument now engaged with the properly-positioned needle within the grid template 140, and with the push plate resting against the grid template 140, the medical instrument can then be operated so as to start inserting seeds into a patient, starting at the deepest location within the prostate (for a particular x,y location on the grid template). Once one or more seeds are implanted into the patient, a handle on the medical instrument is actuated (see FIGS. 2 through 5), which causes the medical instrument to move relative to the sheath unit 115.

The nut box assembly of the medical instrument allows the medical instrument to move relative to the sheath unit 115, while the sheath unit 115 stays at a predetermined distance with respect to the grid template 140. During this time, the grid sheath 100 is being held in place by a doctor. The push plate 170 is in contact with a proximal surface of the grid template 140, to allow the medical instrument to stay in the proper x,y position. The actuation of a handle on the medical instrument moves the medical instrument a particular distance, relative to the sheath unit 115, so as to position the medical instrument to deposit seeds into another location within the patient's prostate. As the medical instrument moves away from the grid template, but with the sheath unit 115 still positioned a predetermined distance away from the grid template, the needle moves in tandem with the medical instrument due to the engagement of the needle to the distal end of the medical instrument. In this manner, seeds can be implanted at various depths, at a particular x,y location of the patient's prostate, in an accurate manner, even though the doctor is physically holding the grid sheath 100 (and thus the medical instrument) in place against the grid template 140.

Once all of the seeds have been deposited at a particular x,y location on the grid template 140 (e.g., a particular hole on the grid template), the doctor can then move the grid sheath 100 (with the medical instrument attached thereto) to thereby position it to engage another needle located at another hole on the grid template 140. During the interim process of moving the needles, buttons 142, 143 are depressed to release the nut box interface from the lead screw (within the body of the medical instrument), to allow reset of the device to the home position relative to the grid sheath.

Figure 6A:
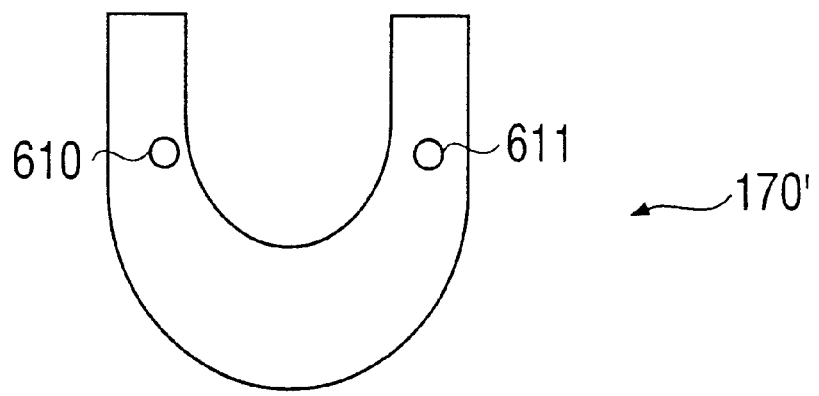
FIGS. 6A and 6B show a front view and a side view, respectively, of a push plate according to a second embodiment of the invention.
Figure 6B:
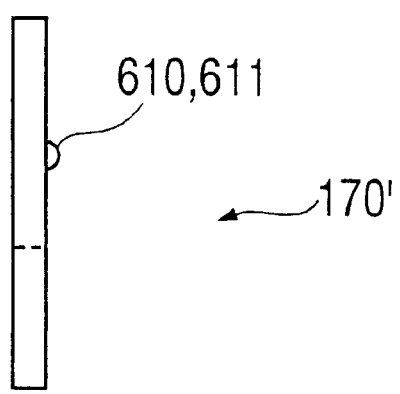

FIGS. 6A and 6B show an element used in a second embodiment of the invention, whereby everything except the push plate is the same. In FIGS. 6A and 6B, the push plate 170 has two bumps 610, 611 on its distal surface. These bumps 611, 612 are sized so that they fit into adjacent left and right holes on the grid template 140, to thereby provide a 'register'function to help the doctor hold the grid sheath (and thereby the medical instrument) in its proper position with respect to the grid template 140.

Figure 7:
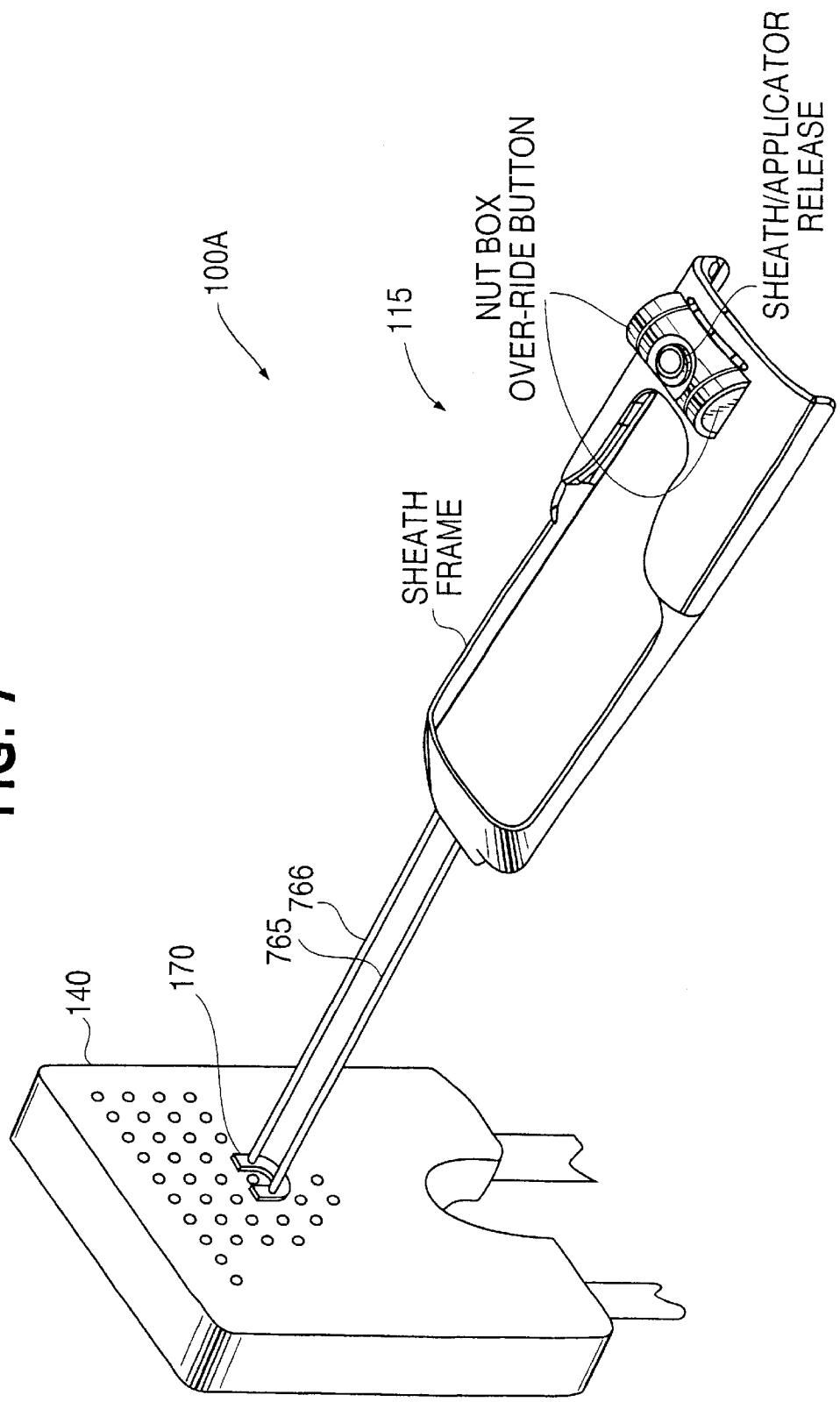
FIG. 7 shows a top perspective view of a grid sheath according to a third embodiment of the invention.

In a grid sheath 100A according to a third embodiment of the invention, as shown in FIG. 7, plate support rods 765, 766 are not capable of telescoping, but rather have a predetermined, fixed length. This predetermined length (e.g., 3 inches) is such that the grid sheath is capable of coupling to a needle sticking out a particular amount (e.g., 3 inches) from the proximal surface of the grid template. In this embodiment, the medical instrument is preferably capable of a larger stroke, such as movement of 4 to 5 inches within the sheath unit, which is larger than the 2¾" to 3" stroke of the medical instrument in the first embodiment, to allow the medical instrument to insert seeds at any depth within a patient's prostate. The grid sheath 100A according to the third embodiment may have a push plate of either the first or the second embodiment.

In the third embodiment, when the medical instrument is engaged with the needle in the grid template, and with the nut box resting against position 128 of the-sheatlh unit 115, the push plate 170 is not in contact with the grid template 140. To get this contact, the user pushes the sheath override buttons 141, 142 to manually move the nut box on the drive screw of the medical instrument, and thus move the medical instrument relative to the sheath unit 115 in a direction towards the grid template 140. This manual movement is performed to place the push plate 170 in intimate contact with the surface of the grid template 140 facing the medical instrument.

Figure 8:
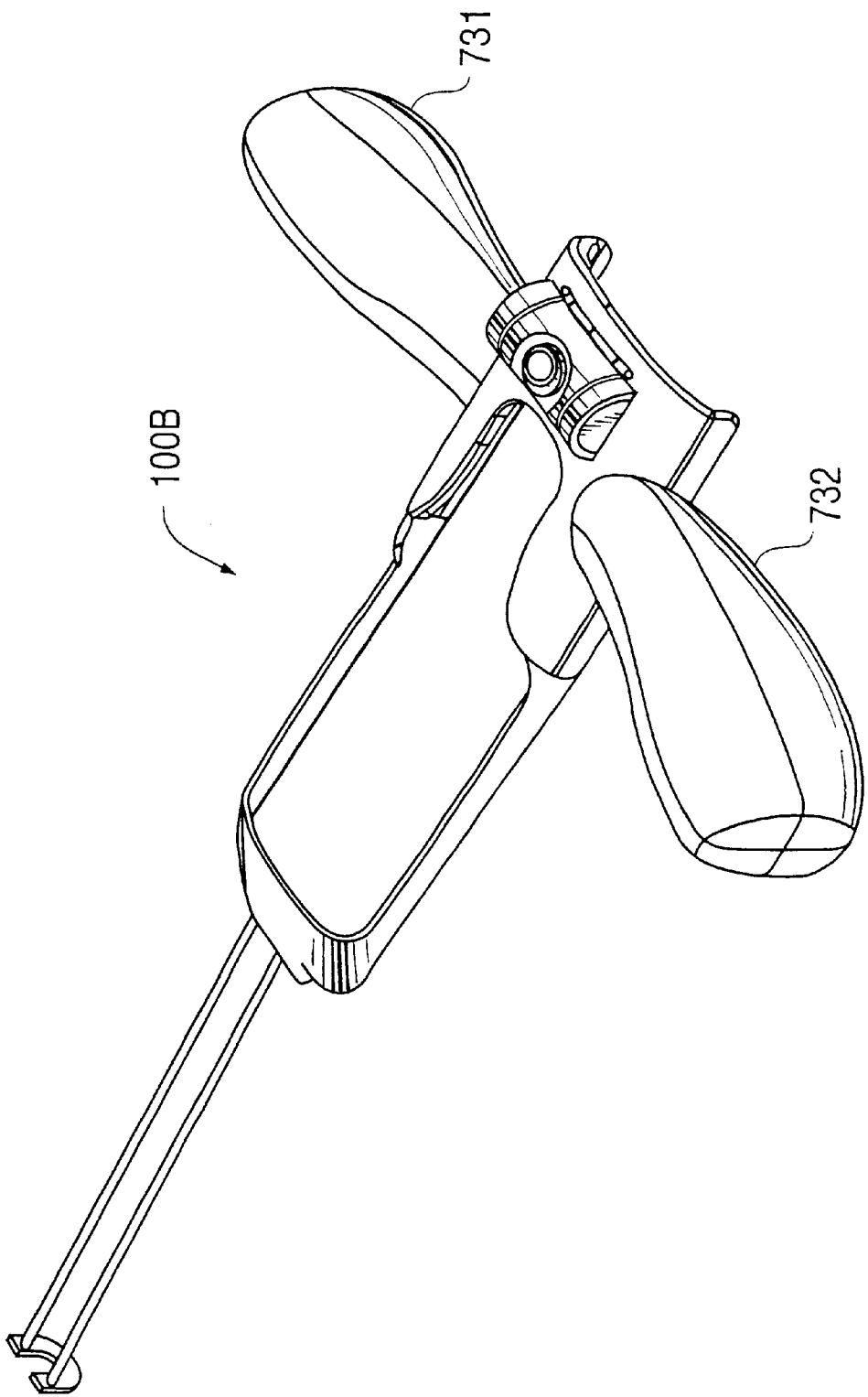
FIG. 8 shows a top perspective view of a grid sheath according to a fourth embodiment of the invention.
Figure 9:
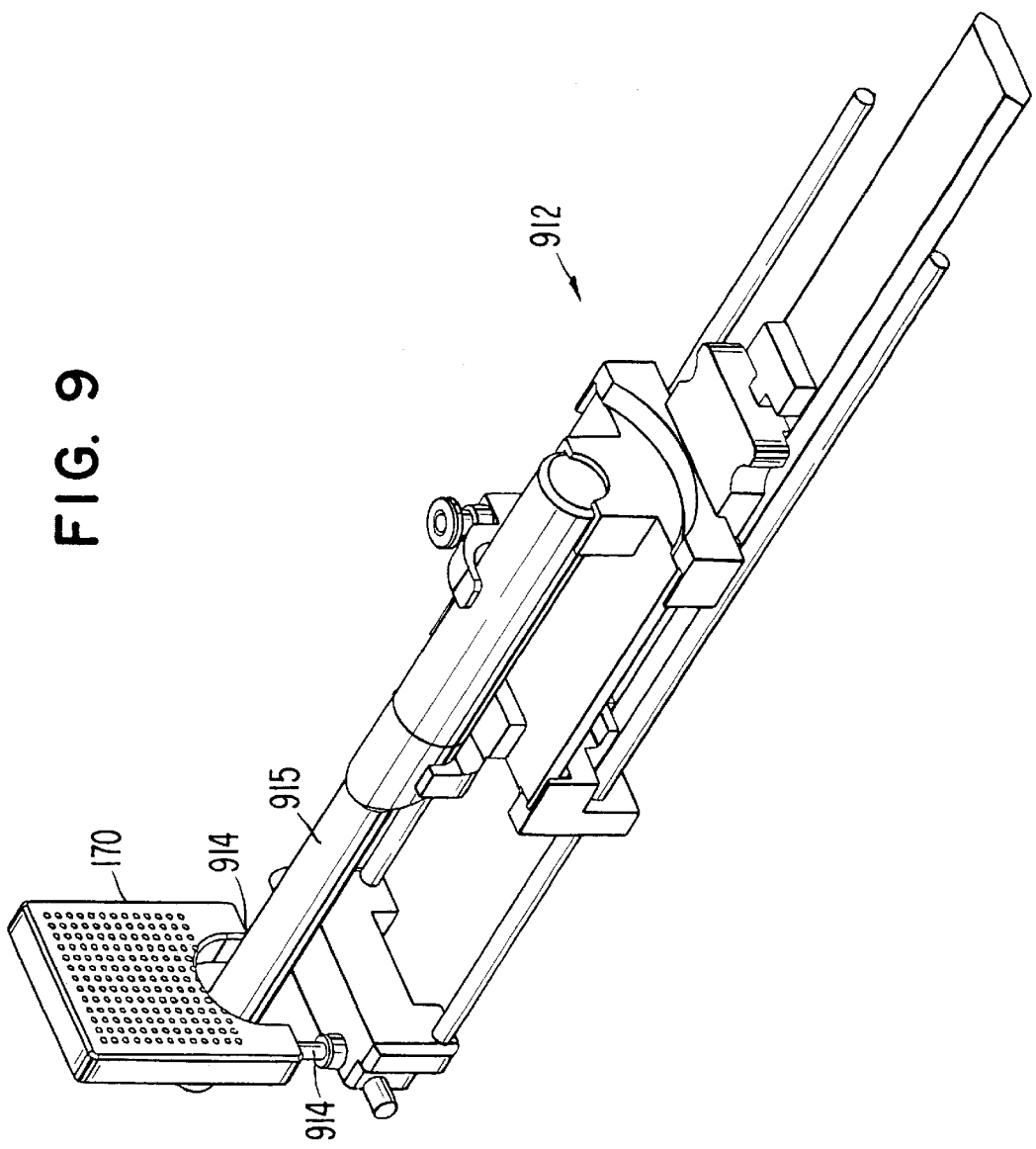
FIG. 9 shows a grid template mounted to a base unit.

FIG. 8 shows a grid sheath 100B according to a fourth embodiment of the invention. The grid sheath 100B is similar to the grid sheath of the first embodiment, but whereby there is included stabilizer handles 731, 732 to allow the user to more securely hold the grid sheath 100B, and thereby the medical instrument attached thereto, in place against the grid template 140. The grid sheath 100B according to the fourth embodimienit may utilize a push plate of either the first or second embodiments, and it may use either the adjustable plate support rods (as in the first or second embodiments), or the fixed plate support rods (as in the third embodiment).

FIG. 10 shows a grid sheath 100C according to a fifth embodiment of the invention. The grid sheath 100C has a proximal frame 1010 and a distal frame 1020, whereby the proximal and distal frames 1010, 1020 are coupled to each other by way of rod telescopes 1030. The rod telescopes 1030 are capable of fitting within cylindrical pathways in the proximal frame 1010, whereby the proximal and distal frames 1010, 1020 can be abutted against each other. Based on the position of a needle disposed in a hole of the grid template 170, the proximal and distal frames 1010, 1020 are positioned away from each other by a predetermined distance, so that the medical instrument can be coupled to the needle (by way of the needle nozzle), and whereby the push plate is retained against the grid template, to provide registration and support of the medical instrument with respect to the grid template 170. A telescope toggle button 1040 is provided on the proximal frames 1010, to allow the proximal and distal frames 1010, 1020 to be moved relative to each other. Once in their proper place, the telescope toggle button 1040 is actuated to lock the proximal and distal frames 1010, 1020 at a predetermined distance away from each other (whereby that predetermined distance may be zero, depending upon the desired position of the medical instrument 700 disposed in the sheath unit) with respect to the grid template 170.

Initially, the medical instrument is placed within the sheath unit, whereby the distal and proximal frames 1010, 1020 are placed in their most compressed position (closest to each other). Now, the medical instrument is coupled to a needle that is fitted within a hole of the grid template, whereby the needle is held in place while the medical instrument is coupled to it. The medical instrument is being manually held in place by the user while it is attached to the needle hub. Now, the telescoping toggle button 1040 is actuated, and the push plate is slid up against the grid template, with the user's free hand. The telescoping toggle button 1040 is toggled to lock the proximal and distal frames 1010, 1020 in fixed position with respect to each other. Now, the seed implanting procedure can begin, whereby the user maintains constant forward tension against the grid template, to maintain the intimate contact of the push plate with the grid template. This keeps the medical instrument in its proper position. Alternatively, this embodiment can include stabilizer handles, as described in an earlier emibodiment. This allows the user ease in holding the medical instrument in place (while it is in the grid sheath). In a further alternative embodiment, instead of a toggle button, a button may be provided on the grid sheath whereby while it is engaged, the proximal and distal frames can be moved relative to each other, and when it is released, the proximal and distal frames are locked in place.

While the present invention has been described above with respect to preferred embodiments, other types of configurations may be possible, while remaining within the spirit and scope of the present invention, as exemplified by the claims. In the preferred embodiments, the plate support rods and the push plate are preferably stainless steel, and the sheath unit is preferably anodized aluminum. Other compounds may be used, as long as they allow for the grid sheath to be reusable and sterilizable (e.g., autoclavable). Other embodiments may include designs consistent with disposable use (e.g., plastic parts).

Also, more than two pins or bumps can be disposed on the push plate 170, 170', in order to provide better means of support of the medical instrument with respect to the grid template. As such, a larger-sized push plate than that shown may be envisioned. Furthermore, while the present invention has been described with respect to implanting seeds into a prostate gland, other types of medical implants into human (or anmnal) organs and the like may be envisioned for the medical instrument coupled to the grid sheath according to the present invention.

What is claimed is:

1. A grid sheath for a medical instrument, comprising:
   a sheath unit configured to couple to a medical instrument, and to allow the medical instrument to move relative to the sheath unit;
   at least one plate support rod that is coupled to a distal end of the sheath unit; and
   a push plate that is coupled to a distal end of the at least one plate support rod, wherein the push plate is configured to abut against a grid template to allow an operator to manually operate the medical instrument while maintaining the medical instrument in a particular x, y location with respect to the grid template,
   wherein the push plate has at least one bump or pin on a distal surface thereof, so as to fit within a hole of the grid template that is adjacent to one of a plurality of holes of the grid template.

2. The grid sheath according to claim 1, wherein the grid template includes a plurality of holes in a matrix configuration,
   wherein the grid template is configured to accept at least one needle that is positioned in at least one of the plurality of holes, and
   wherein a distal end of the medical instrument includes a needle engagement mechanism to engage with the needle.

3. The grid sheath according to claim 2, wherein the push plate has a U-shape and is configured to be positioned around the one of the plurality of holes, to thereby support the medical instrument against the grid template while seeds are implanted into a patient.

4. The grid sheath according to claim 1, wherein the at least one plate support rod is adjustable in length.

5. A grid sheath for a medical instrument, comprising:
   a sheath unit configured to couple to a medical instrument, and to allow the medical instrument to move relative to the sheath unit;
   at least one plate support rod that is coupled to a distal end of the sheath unit; and
   a push plate that is coupled to a distal end of the at least one plate support rod,
   wherein the medical instrument has a needle nozzle that allows for a needle to be engaged with the medical instrument,
   wherein the at least one plate support rod is of a size such that the push plate is not in contact with the grid template when the needle is engaged with the medical instrument, and
   wherein either the plate support rod is capable of being lengthened to make the push plate be in contact with a surface of the grid template, or the medical instrument is capable of moving an amount relative to the sheath unit so that the push plate is put in contact with the surface of the grid template,
   and wherein the push plate has at least one bump or pin on a distal surface thereof, so as to fit within a hole of the grid template that is adjacent to one of a plurality of holes of the grid template.

6. The grid sheath according to claim 5, wherein the push plate has a U-shape and is configured to be positioned around one of a plurality of holes of the grid template, to thereby support the medical instrument against the grid template while seeds are implanted into a patient by way of the medical instrument and the needle.

7. A grid sheath for a medical instrument, comprising:
   a sheath means that allows the medical instrument to move relative to the sheath means;
   a support means that is coupled to a distal end of the sheath means; and
   a fixing means attached to the support means that allows an operator to manually operate the medical instrument while maintaining the medical instrument in a particular x, y location.

8. The grid sheath of claim 7, wherein said fixing means comprises a push plate configured to abut against a grid template to allow an operator to manually operate the medical instrument while maintaining the medical instrument in a particular x, y location with respect to the grid template.

9. The grid sheath of claim 8, wherein the push plate has at least one bump or pin on a distal surface thereof, so as to fit within a hole of the grid template that is adjacent to one of a plurality of holes of the grid template.

10. A grid sheath for a medical instrument, comprising:
    a means for sheathing that allows the medical instrument to move relative to the means for sheathing;
    a means for supporting coupled to a distal end of the means for sheathing; and
    a means for fixing attached to the means for supporting that allows an operator to manually operate the medical instrument while maintaining the medical instrument in a particular x, y location.

11. The grid sheath of claim 10, wherein the means for fixing comprises a push plate configured to abut against a grid template to allow an operator to manually operate the medical instrument while maintaining the medical instrument in a particular x, y location with respect to the grid template.

12. The grid sheath of claims 11, wherein the push plate has at least one bump or pin on a distal surface thereof, so as to fit within a hole of the grid template that is adjacent to one of a plurality of holes of the grid template.

* * * * *